United States Patent [19]

Prater

[11] Patent Number: 4,957,442
[45] Date of Patent: Sep. 18, 1990

[54] APPARATUS AND METHOD FOR ASSISTING A DISABLED PERSON TO HAND WRITE WITH A WRITING INSTRUMENT

[76] Inventor: Stephen J. Prater, 444 S. Fenton Ave., Indianapolis, Ind. 46219

[21] Appl. No.: 425,943

[22] Filed: Oct. 24, 1989

[51] Int. Cl.⁵ .................. G09B 11/00; B43L 13/00; B43L 15/00
[52] U.S. Cl. ........................... 434/166; 401/6; 623/65; 272/67
[58] Field of Search .................. 434/112, 162, 166; 272/67, 68, 117, 119, 127; 401/6, 7, 8; 414/1, 9; 2/159, 160; 623/57, 65

[56] References Cited

U.S. PATENT DOCUMENTS

| | | | |
|---|---|---|---|
| 563,107 | 6/1896 | Watt | 434/166 |
| 617,169 | 1/1899 | Lanier | 434/166 |
| 2,697,416 | 12/1954 | Simmons | 401/8 X |
| 2,748,474 | 6/1956 | Brown | 401/6 X |
| 2,819,081 | 1/1958 | Touraine | 272/127 X |
| 3,373,509 | 3/1968 | Brass | 401/6 X |
| 3,629,867 | 12/1971 | Taylor | 2/160 |
| 4,035,865 | 7/1977 | McRae et al. | 401/6 X |
| 4,447,912 | 5/1984 | Morrow | 2/160 X |
| 4,523,781 | 6/1985 | Brody | 623/65 X |
| 4,602,885 | 7/1986 | Bischoff et al. | 401/8 X |
| 4,740,126 | 4/1988 | Richter | 414/1 X |
| 4,796,306 | 1/1989 | Mitchell | 2/160 |

FOREIGN PATENT DOCUMENTS

| | | | |
|---|---|---|---|
| 316851 | 8/1929 | United Kingdom | 401/7 |
| 1157623 | 6/1969 | United Kingdom | 401/6 |

Primary Examiner—Richard J. Apley
Assistant Examiner—J. L. Doyle
Attorney, Agent, or Firm—Woodard, Emhardt, Naughton Moriarty & McNett

[57] ABSTRACT

An apparatus and method for assisting the disabled to handwrite. The apparatus comprises a stabilizing weight member. The stabilizing weight member is attached to the hand by a glove or other means. The weight member has angled finger grip protrusions for forming slots for the fingers of the hand to rest in and to hold and conrol the movement of the weight member. The weight member has a roller ball socket in its underside in which is rotatably mounted a roller ball. The weight member also has a writing instrument holder which holds the writing instrument so that it will write on a writing surface when the roller ball is against that surface. The hand moves the weight member by rolling the roller ball against the writing surface so that the writing instrument writes.

17 Claims, 2 Drawing Sheets

APPARATUS AND METHOD FOR ASSISTING A DISABLED PERSON TO HAND WRITE WITH A WRITING INSTRUMENT

BACKGROUND OF THE INVENTION

1. Field of the Invention

The field of the invention is apparatus for assisting disabled persons to perform functions that are routinely performed by non-disabled persons. More particularly, the invention relates to assisting persons with disabilities which make it difficult for them to handwrite.

2. Description of the Prior Art

The inventor of this invention is thirteen years old and is disabled by spina bifida which disables his legs. He created this invention for a thirteen year old class mate that has cerebral palsy. At the time of his invention he was not aware of any apparatus that addressed the problems of his class mate. Her cerebral palsy made it very difficult for her to control her hand and handwrite in school because of occasional spasms. The prior art was that she tried to write by holding the pen or pencil in her hand and overcoming her disability by stabilizing the pen or pencil with just her limited muscle coordination.

The present invention improves over the prior art by providing an apparatus and method which helps people with disabilities such as cerebral palsy or severe arthritis to hand write without relying totally on their impaired coordination and muscles

SUMMARY OF THE INVENTION

The invention is an apparatus and method for assisting the disabled to handwrite on a writing surface. The apparatus includes a stabilizing weight member. A gliding means is attached to the weight member. The gliding mean being for gliding against a writing surface so that the weight member remains disposed above and supported on the writing surface. The weight member also has a writing instrument holder means attached to it. The holder means is for holding a writing instrument so that the writing end of the instrument extends to write on the writing surface when the gliding means is gliding against the writing surface. The weight member also has hand attachment means mounted to the top side of the weight member. The hand attachment means is for attaching the weight member to a hand.

The method of the invention is to use a weight member that has a gliding means, writing instrument holder means and hand attachment means to assist a disabled person to handwrite. The above described apparatus is attached to the hand. A writing instrument is inserted into the writing instrument holder. The hand attached to the weight member is moved so that the gliding means is against the writing surface. Then the hand attached to the weight member is moved so that the gliding means glides against the writing surface and the writing instrument writes on the surface. Thus, an object and advantage of the invention is that a disabled person may more easily handwrite. Further objects and advantages of the invention are described hereafter.

BRIEF DESCRIPTION OF THE DRAWINGS

FIG. 1 is a side view of the preferred embodiment of this invention with a partial cross sectional view of the roller ball assembly.

FIG. 2 is a top view of the preferred embodiment of the invention shown in FIG. 1.

FIG. 3 is a bottom view of the preferred embodiment of the invention shown in FIG. 1.

DESCRIPTION OF THE PREFERRED EMBODIMENT

Figure 1:
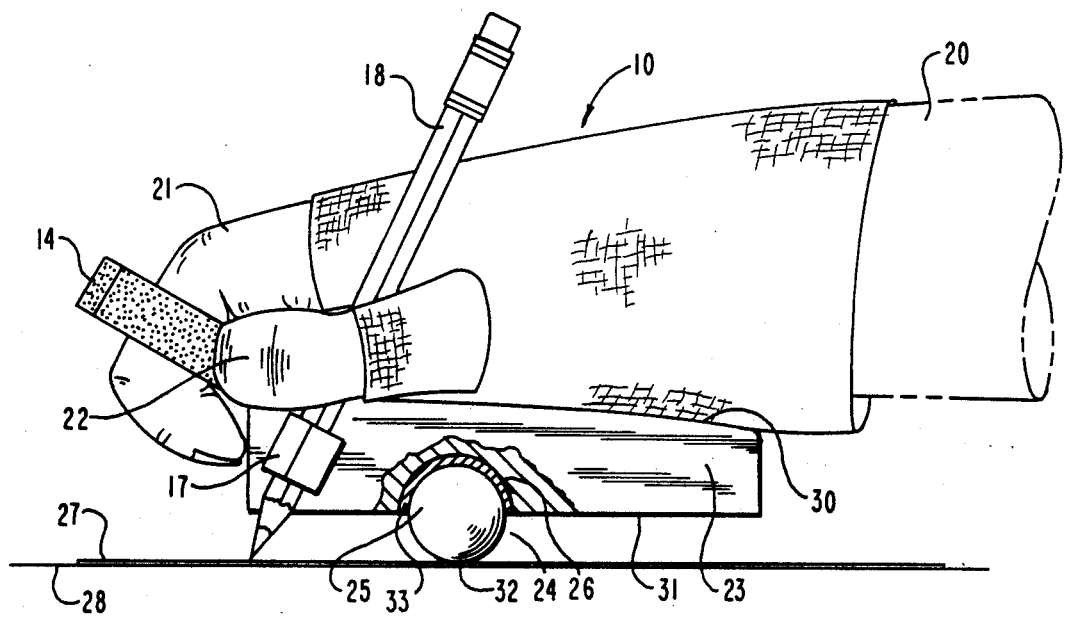
FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 shows the preferred embodiment of the handwriting stabilizer 10 of the present invention. The handwriting stabilizer 10 has a stabilizing weight member 23. The stabilizing weight member 23 is made to have a weight that corresponds to the strength and coordination of the particular disabled person that will be using the stabilizer 10. For example, a version for a thirteen year old girl with cerebral palsy was made to have a weight member 23 weight of one and one-half pounds. Other weights will be tailored to the specific needs and comfort of the particular disabled person. Suitably the weight should be readily manipulated by that person without undue strain. However, the weight should be enough that they recognize its presence so that it will act to stabilize the movement of their hand to retain the weight against the writing surface. Accordingly, the weight member 23 can be made of a plurality of materials.

As shown in FIG. 1, the weight member 23 has a top side 30 and a bottom side 31. A gliding means is provided by a roller ball assembly 24 disposed in the bottom 31 of the weight member 23. The roller ball assembly 24 is the preferred embodiment. However, it is recognized that other suitable gliding means can be used to perform the same function as the roller ball assembly 24. The roller ball assembly 24 has a socket 26 that is in the bottom of the weight member 23 as shown in cross section in FIG. 1. The socket 26 has a socket surface 33 which is of a material to reduce friction between that surface and the roller ball 25 that is rotatably mounted in the socket 26.

The gliding means provides a means for bringing the weight member 23 in proximity with the surface 28 where the writing paper 27 is disposed. One of the functions of the gliding means is that it serves to separate the bottom 31 of the weight member 23 from paper 27. In the preferred embodiment the separation is the amount that the roller ball 25 extends beyond the bottom 31 to the point at which the ball 25 rests against the writing surface and paper 32. The gliding means thus, in a vertical direction, serves as a means for placing the weight member 23 in proximity to the paper 27. The weight of the weight member 23 is thus supported by the gliding means, here the ball 25, as it rests against the surface 28. Thus the user no longer has to substantially support the weight 23. However, because of the weight 23 the user will more easily keep the ball 25 in contact with the writing surface 28 and not lift the apparatus from the paper. Thus stability is provided in a vertical direction.

The gliding means also functions to allow the user to move the weight 23 above the paper 27 while maintaining roughly the same proximity. The gliding means glides against the writing surface and thereby reduces friction. In the preferred embodiment, the roller ball 25 rotates in the socket 26 as the user moves the weight 23 over the paper and writing surface. The user thus has a stabilized apparatus 10 that readily moves over the paper.

The weight member 23 also has a writing instrument holder 17. In the preferred embodiment, the writing instrument holder 17 holds the writing instrument 18, as shown in FIG. 1, at an angle to the plane of the writing surface 28 and the weight member 23 is parallel to the writing surface 28. The writing instrument holder 17 has a writing instrument passageway 19. The writing instrument 18 is inserted in this passageway 19. The diameter of the passageway 19 is made so that the writing instrument 18 will friction fit in the passageway. Thus the writing instrument 18 will not readily slide in the passageway 19. Thus disposed, the user does not have to grip the writing instrument 18 with their hand when writing. Many disabled persons with hand disabilities cannot readily hold a writing instrument. The present invention alleviates this problem.

Figure 2:
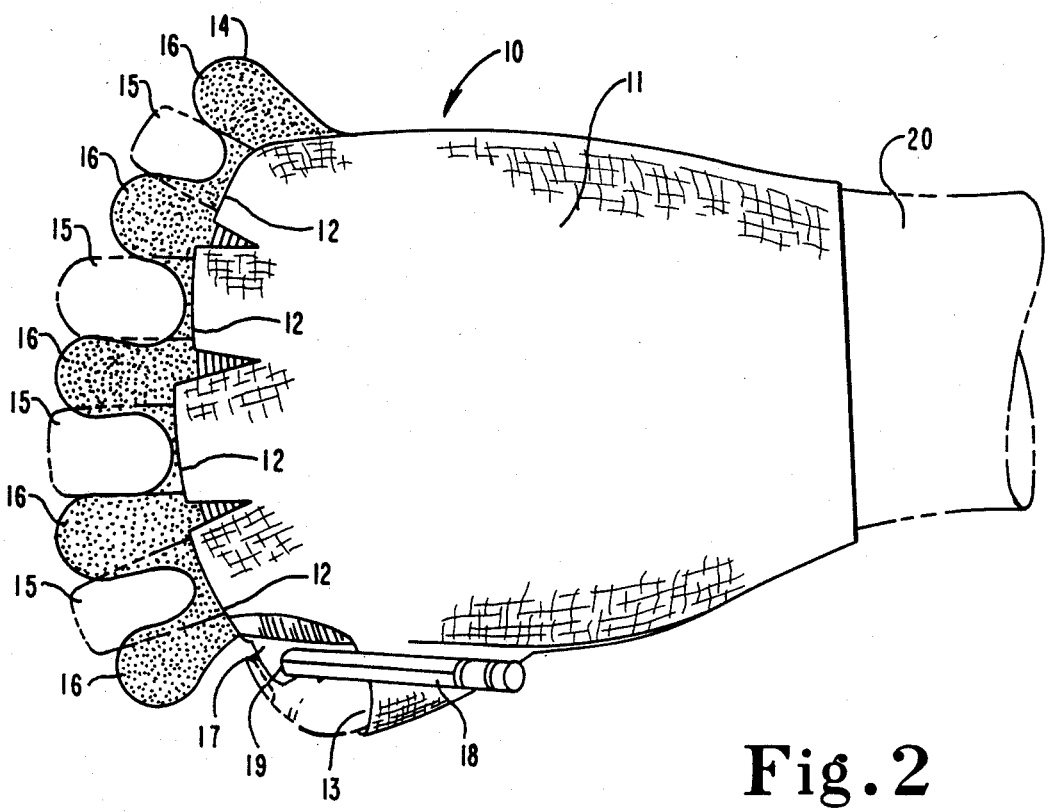
FIG. 2.
Figure 3:
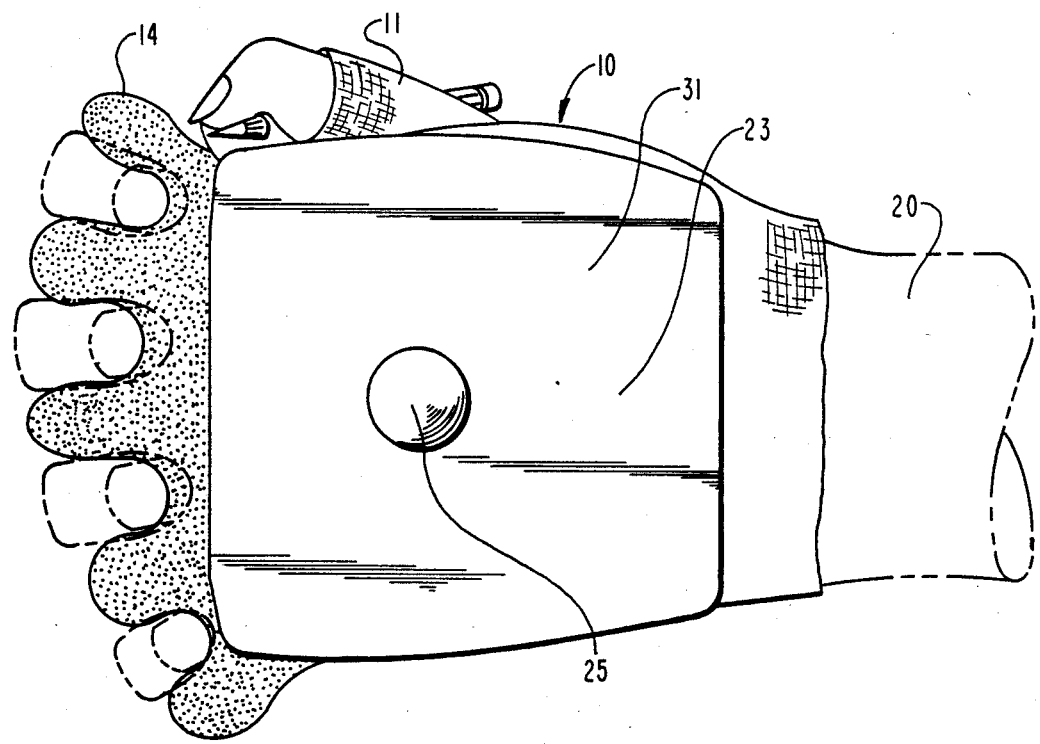
FIG. 3.

As shown in FIGS. 2 and 3 the weight member 23 has a finger grip 14 extending from the end adjacent the writing instrument holder 17. The finger grip 14 has a plurality of finger grip protrusions 16 which form finger slots 15. The fingers of the user are disposed in these slots 15 as shown in FIGS. 1, 2 and 3. As shown in FIG. 1 the finger grip 14 is angled up from the horizontal plane of the weight 23 and the writing surface 28.

Attached to the top 30 of the weight member 23 is a glove 11. The glove 11 has finger openings 12 and thumb opening 13. The glove serves as a hand attachment means so that the weight member 23 can be attached to the hand as shown in FIGS. 1, 2 and 3. It is contemplated that a strap or other hand attachment means could be used instead of the glove. The glove 11 is used in the preferred embodiment. Again, many disabled persons with hand disabilities find it difficult to hold a writing apparatus. Thus, use of the glove or equivalent hand attachment means alleviates this problem.

With the apparatus 10 as shown in the FIGS. 1, 2 and 3 and as described above, the user can write as will be described. The user places their hand 20 inside of the glove 11 so that their fingers 21 extend through the openings 12 and their thumb 22 through the opening 13. The fingers then extend through the slots 15 and grip the finger grip 14 as shown in FIG. 1. A writing instrument 18 is inserted in the holder 17 so that it extends the appropriate amount beneath the surface 31 of the weight 23 so that it will write when the roller ball 25 is placed against the paper 27 on the surface 28. The user then places the ball 25 against the paper 27 and writing surface 28. By rolling the ball 25 against the paper 27 the writing instrument 18 will write on the paper as shown in FIG. 1. The weight 23 helps to stabilize the user's hand and the roller ball 25 helps to ease movement of the weight and to maintain the precision of the motion.

While the invention has been illustrated and described in detail in the drawings and foregoing description, the same is to be considered a illustrative and not restrictive in character, it being understood that only the preferred embodiment has been shown and described and that all changes and modifications that come within the spirit of the invention ar desired to be protected.

What is claimed is:

1. An apparatus for assisting the disabled to handwrite, said apparatus comprising:
   a stabilizing weight member having a top side and a bottom side, and a roller ball socket in said bottom side;
   a roller ball rotatably mounted in said roller ball socket;
   writing instrument holder means attached to said weight member, said holder means being for holding a writing instrument so that the writing end of said instrument extends beyond said bottom side;
   said writing instrument holder means includes a holder protrusion extending from the side of said weight member, said holder protrusion having a writing instrument passageway; and
   hand attachment means mounted to the top side of said weight member, said hand attachment means being for attaching said weight member to a hand.

2. The apparatus of claim 1 further comprising finger grip means attached to an end of said weight member adjacent said writing instrument holder means, said finger grip means being for placing the fingers of the hand to assist in holding and controlling the movement of the weight member.

3. The apparatus of claim 2 wherein said finger grip means includes a plurality of finger grip protrusions extending from said weight member and said finger grip protrusions define finger slots.

4. The apparatus of claim 3 wherein said top of said weight member is in a first plane and said finger grip protrusions extend from said weight member in a second plane, said second plane intersecting said first plane.

5. The apparatus of claim 1 wherein said hand attachment means includes a glove, the bottom of said glove being attached to the top of said weight member.

6. The apparatus of claim 5 wherein said glove has a plurality of finger openings and a thumb opening.

7. The apparatus of claim 5 further comprising finger grip means attached to an end of said weight member adjacent said writing instrument holder means, said finger grip means being for placing the fingers of the hand to assist in holding and controlling the movement of the weight member.

8. The apparatus of claim 7 wherein said finger grip means includes a plurality of finger grip protrusions extending from said weight member and said finger grip protrusions define finger slots.

9. The apparatus of claim 8 wherein said top of said weight member is in a first plane and said finger grip protrusions extend from said weight member in a second plane, said second plane intersecting said first plane.

10. The apparatus of claim 9 wherein said glove has a plurality of finger openings and a thumb opening.

11. An apparatus for assisting the disabled to handwrite on a writing surface, said apparatus comprising:
    a stabilizing weight member;
    a gliding means attached to said weight member, said gliding mean being for gliding against a writing surface so that said weight member remains disposed above said writing surface;
    writing instrument holder means attached to said weight member, said holder means being for holding a writing instrument so that the writing end of said instrument extends to said writing surface when said gliding means is gliding against said writing surface;

hand attachment means mounted to the top side of said weight member, said hand attachment means being for attaching said weight member to a hand; and said hand attachment means includes a glove, the bottom of said glove being attached to the top of said weight member.

12. The apparatus of claim 11 wherein said gliding means includes a roller ball socket in the bottom side of said weight member and a roller ball rotatably mounted in said roller ball socket.

13. The apparatus of claim 12 further comprising finger grip means attached to an end of said weight member adjacent said writing instrument holder means, said finger grip means being for placing the fingers of the hand to assist in holding and controlling the movement of the weight member.

14. The apparatus of claim 11 further comprising finger grip means attached to an end of said weight member adjacent said writing instrument holder means, said finger grip means being for placing the fingers of the hand to assist in holding and controlling the movement of the weight member.

15. The apparatus of claim 14 wherein said finger grip means includes a plurality of finger grip protrusions extending from said weight member and said finger grip protrusions define finger slots.

16. The apparatus of claim 15 wherein said top of said weight member is in a first plane and said finger grip protrusions extend from said weight member in a second plane, said second plane intersecting said first plane.

17. A method for stabilizing the hand of a disabled person to help them handwrite on a writing surface, said method comprising the steps:
(1) gripping with the hand a stabilizing weight member having a plurality of finger grip protrusions defining finger slots by placing the fingers of the hand in the finger slots of the stabilizing weight member, said stabilizing weight member having a gliding means for gliding against a writing surface so that said weight member remains disposed above said writing surface and said weight having a writing instrument holder means attached to said weight member, said holder means being for holding a writing instrument so that the writing end of said instrument extends to said writing surface when said gliding means is gliding against said writing surface;
(2) inserting a writing instrument into said writing instrument holder;
(3) moving the hand that is gripping the weight member so that the gliding means is against the writing surface; and
(4) moving the hand that is gripping the weight member so that the gliding means glides against said writing surface and said writing instrument writes on said surface.

* * * * *